United States Patent [19]

Carter et al.

[11] Patent Number: 4,975,437
[45] Date of Patent: Dec. 4, 1990

[54] ISOMERS OF 1-AZABICYCLO(2.2.2)OCT-3-YL 1,4-DIHYDRO-2,6-DIMETHYL-4-(3-NITROPHENYL)-5-NITROPYRIDINE-3-CARBOXYLATE

[75] Inventors: John P. Carter, Baltimore; Waclaw J. Rzeszotarski, Millersville, both of Md.

[73] Assignee: Marion Laboratories, Inc., Kansas City, Mo.

[21] Appl. No.: 450,736

[22] Filed: Dec. 14, 1989

[51] Int. Cl.⁵ .................. A61K 31/455; C07D 401/14
[52] U.S. Cl. ..................................... 514/305; 546/137
[58] Field of Search .......................... 546/137; 514/305

[56] References Cited

PUBLICATIONS

L. Noronha-blob et al., biochem and Biophys. Res. Commun. 147, 182–188, 1987.

*Primary Examiner*—Jane T. Fan
*Attorney, Agent, or Firm*—Theresa M. Gillis

[57] ABSTRACT

The four stereoisomers are disclosed having the formula:

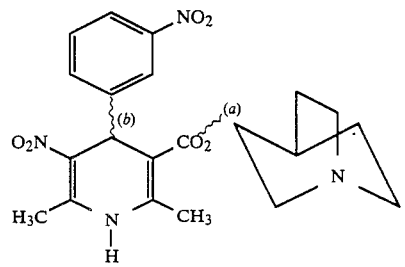

in which the asymmetric centers a and b are the same or different. The compounds are derived from the (+) and (−) alcohols and the (+) and (−) dihydropyridines and have either the absolute R or S configuration. Also disclosed are pharmaceutical compositions comprising an effective amount of the compounds in a pharmaceutically acceptable carrier and methods for producing cardiotonic activity using the compositions.

8 Claims, No Drawings

ISOMERS OF 1-AZABICYCLO(2.2.2)OCT-3-YL 1,4-DIHYDRO-2,6-DIMETHYL-4-(3-NITROPHENYL)-5-NITROPYRIDINE-3-CARBOXYLATE

BACKGROUND OF INVENTION (a) Field of the Invention

Isomers of 1-azabicyclo[2.2.2]oct-3-yl 1,4-dihydro-2,6-dimethyl-4-(3-nitrophenyl)-5-nitropyridine-3-carboxylate and their nontoxic acid addition salts are useful calcium agonists having utility as cardiotonics and in the treatment of cardiovascular disorders such as congestive heart failure.

(b) State of the Art

The essential role of calcium ions in the contraction of muscle has been well known since the last century. In contrast to skeletal muscle in which the actions of calcium ions occur within the cell, the operation of smooth and cardiac muscle depends to a large extent on the extracellular concentration of calcium. Therefore, the regulation of extracellular calcium plays a crucial role in the treatment of several cardiovascular disorders.

The most common agents used to regulate these ions are calcium antagonists or calcium channel blockers. Simplistically, these are compounds that "slow" the entry of calcium ions into the cell and thereby reduce the force or contractility of cardiac muscle resulting in the lowering of blood pressure. Additionally, these agents find use in the treatment of angina caused by abnormal vasoconstriction of coronary arteries and classical effort associated angina.

Another much smaller class of agents that regulate these ions are calcium agonists or calcium channel activators. These compounds promote the movement of calcium ions through the cell wall and therefore increase contractility. They may be useful in the treatment of disorders of lessened cardiac output such as congestive heart failure. Alternatively, they may be used as tools in the pharmacological study of calcium channels.

Methyl 1,4-dihydro-2,6-dimethyl-5-nitro-4-(2-trifluoromethylphenyl)-3-pyridine carboxylate [BAY K 8644, M. Schramm, G. Thomas, R. Toward and G. Frankowiak, Nature, 303, 535 (1983), German Patent DE No. 3,447,169 and European Pat. No. 186 028 A2], whose pharmacological characteristics have been thoroughly studied, is a prototype of the dihydropyridine calcium agonists. It causes potent positive inotropic effects. H. Rogg et al. [Biochem. Biophys. Res. Commun. 118: 842, 1984, European Pat. Nos. 111,453 and 111,455] have disclosed ethyl 4-[2-(difluoromethoxy)-phenyl]-1,4,5,7-tetrahydro-2-methyl-5-oxofuro[3,4-b]pyridine-3-carboxylate (CGP 28392) and described its ability to increase in a dose-dependent manner the concentration of extracellular calcium ions.

The effects of stereochemistry on the biological actions of this type of pharmacological agent have been described by R. P. Hoff, U. T. Ruegg, A. Hof and A. Vogel [J. Cardiovasc. Pharmacol., 7, 689 (1985), British Pat. No. 2,148,895 and German Pat. No. 3,438 884]. Racemic 2-propyl 4-(4-benzofurazanyl)-1,4-dihydro-2,6-dimethyl-5-nitropyridine-3-carboxylate (202-792) enhanced contractions of rabbit aortic rings at low levels of depolarization, the typical result of calcium agonism, but inhibited contraction and radioactive calcium uptake at high levels of depolarization. The R enantiomer also inhibited contraction and radioactive calcium uptake and showed no stimulant activity. The S enantiomer, however, shifted the concentration-response curve for depolarization-induced contraction in an almost parallel fashion to the left; it enhanced contraction. This compound enhanced radioactive calcium uptake dependently at all levels of depolarization. Thus, the stereoisomers of this dihydropyridine behave as a calcium entry blocker or a calcium entry enhancer, depending on their stereochemistry.

Similar results have been described for ethyl β-amino-4-(2-chlorophenyl)-1,4-dihydro-6-methylpyridine-3-carboxylate [H 160/51; U.S. Pat. No. 4,532,248 and German Pat. No. 3,130,041] by P. Gjorstrup, H. Harding, R. Isaksson and C. Westerlund [Eur. J. Pharmacol., 122, 357 (1986)]. The optical isomers of this dihydropyridine were found to have opposing actions in the cat papillary muscle and rat portal vein. The (+) enantiomer inhibited the actions of calcium ions and therefore decreased the force of contraction of these tissues, whereas the (−) enantiomer stimulated calcium's effects and was found to significantly increase the force of contraction.

As can easily be seen, a variety of structurally diverse dihydropyridines possess calcium agonist activity. In fact, P. Gjorstrup et al. [Eur. J. Pharmacol., 122, 357–361, (1986)] states that "The structural features responsible for a specific fit of an agonist (to the calcium channels) seem more obscure."

Relatively few calcium channel modifiers with a basic amine in the alkyl portion of a 1,4-dihydropyridine-3-carboxylic acid ester have been described. The vascular and cardiac effects of another calcium agonist 2-(2-pyridyl)ethyl-3-anilinocarbonyl-4-(2-chlorophenyl)-1,4-dihydro-2,6-dimethylpyridine-3-carboxylate (YC-170), have been described by Y. Hattori, H. Nakaya, N. Tohse and M. Kanno [J. Pharmacol. Exp. Ther., 238, 670]. This agent produced a positive inotropic effect in isolated guinea pig atrium and induced contraction in isolated rabbit aortic strips. However, this agonist caused a decrease in contractile tension in the atrium partially depolarized with a low concentration of potassium and produced a relaxant effect on the aorta precontracted by a high concentration of potassium. These results indicate that YC-170 may behave not only as a calcium agonist, but also as a calcium antagonist depending on the cellular membrane potential. Esters of 1-azabicyclo[2.2.2]octan-3-ol with aryl or aralkylcarboxylic acids generally have calcium channel blocking activity (L. Noronha-Blob, C. Richard and D. C. U'Prichard, Biochem. and Biophys Res. Commun., 147, 182–188, 1987).

The novel isomers of 1-azabicyclo[2.2.2]oct-3-yl 1,4-dihydro-2,6-dimethyl-4-(3-nitrophenyl)-5-nitropyridine-3-carboxylate described herein are potent calcium channel agonists as evidenced by their ability to potentiate the physiological movement of calcium ions and to enhance calcium-evoked smooth muscle contractility. These actions indicate usefulness of these isomers as cardiotonic agents and in cardiac disorders such as congestive heart failure.

SUMMARY OF THE INVENTION

The invention provides a group of four stereoisomers of the formula I.

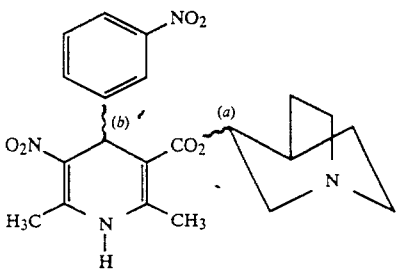

wherein the asymmetric centers a and b may be the same or different and have either the absolute R or S configuration. The invention also relates to the pharmaceutically acceptable salts of the foregoing compounds, to pharmaceutical compositions containing such compounds, and to their use in producing cardiotonic activity and in the treatment of congestive heart failure.

DETAILED DESCRIPTION OF THE INVENTION

The compounds of this invention are novel isomers of 1-azabicyclo[2.2.2]oct-3-yl 1,4-dihydro-2,6-dimethyl-4-(3-nitrophenyl)-5-nitropyridine-3-carboxylate of the above formula and their pharmaceutically acceptable salts. The compounds are effective calcium channel agonists which makes them useful as cardiotonic agents and for the treatment of cardiovascular disorders such as congestive heart failure. The invention thus includes pharmaceutical compositions intended for such uses which comprise an effective amount of the individual isomers and a pharmaceutically acceptable carrier. The invention also includes methods of using such compositions as calcium channel agonists and to treat a variety of cardiovascular disorders.

The preferred compound of this invention is (+a, −b) 3-azabicyclo[2.2.2]oct-3-yl 1,4-dihydro-3,6-dimethyl-4-(3-nitrophenyl)-5-nitropyridine-3-carboxylate.

The compounds of this invention may be used in the form of a pharmaceutically acceptable acid addition salt having the utility of the free base. Such salts, prepared by methods well known to the art, are formed with both inorganic or organic acids, for example: maleic, fumaric, benzoic, ascorbic, pamoic, succinic, bismethylenesalicyclic, methanesulfonic, ethanedisulfonic, acetic, oxalic, propionic, tartaric, salicyclic, citric, gluconic, lactic malic, mandelic, cinnamic, citraconic, aspartic, stearic, palmitic, itaconic, glycolic, p-aminobenzoic, glutamic, benzenesulfonic, hydrochloric, hydrobromic, sulfuric, cyclohexylsulfamic, phosphoric and nitric acids. To the extent the compounds of the invention may exist as optical isomers, both isomers and the racemic mixture are to be understood to be included in the invention. In addition, all possible other isomeric forms of the compounds of the invention are within the ambit of this invention.

The compounds of this invention may be administered orally or parenterally in conventional dosage unit forms such as tablets, capsules, injectables, aerosols, or the like, by incorporating the appropriate dose of a compound of the indicated formula with carriers according to accepted pharmaceutical practices.

Preferably, a compound or an acid addition salt thereof is administered orally to an animal organism in a tablet or capsule comprising an amount sufficient to produce the desired activity. Each dosage unit will contain the active ingredient in an amount of about 10 mg to about 400 mg, preferably from about 30 mg to about 200 mg. Advantageously equal doses will be administered 2 to 4 times daily with the daily dosage regimen being about 60 mg to about 600 mg, preferably from about 100 mg to about 300 mg.

The pharmaceutical carrier employed may be, for example, either a solid or liquid. Exemplary of solid carriers are lactose, terra alba, sucrose, talc, gelatin, agar, pectin, acacia, magnesium stearate, stearic acid and the like. Exemplary of liquid carriers are syrup, peanut oil, olive oil, water and the like. Similarly, the carrier or diluent can include any time delay material well known to the art, such as glyceryl monostearate or glyceryl distearate alone or with a wax.

A wide variety of pharmaceutical forms can be employed. Thus, if a solid carrier is used, the preparation can be tableted, placed in a hard gelatin capsule in powder or pellet form, or in the form of a troche or lozenge. The amount of solid carrier will vary widely but preferably will be about 25 mg to about 1 g. If a liquid carrier is used, the preparation will be in the form of a syrup, emulsion, soft gelatin capsule, sterile injectable liquid such as an ampule, or an aqueous or nonaqueous liquid suspension.

The compounds of the invention can be prepared by esterification of the enantiomers of 1,4-dihydro-2,6-dimethyl-4-(3-nitrophenyl)-5-nitropyridine carboxylic acid with the enantiomers of 1-azabicyclo[2.2.2]octan-3-ol (3-quinuclidinol). The acid was prepared by condensation of 3-nitrobenzaldehyde with D-butylamine to give an imine which upon further condensation with 1-nitro-2-propanone affords 4-(3-nitrophenyl)-3-nitro-3-buten-2-one. Cycloaddition of this ketone to 2-cyanoethyl 3-aminobut-2-enoate, prepared by amination of 2-cyanoethyl acetoacetate, affords the 2-cyanoethyl ester of 1,4-dihydro-2,6-dimethyl-4-(3-nitrophenyl)-5-nitropyridine carboxylic acid from which the acid is obtained by alkaline hydrolysis. Resolution of the acid is achieved by recrystallization of the brucine salt from methanol. The enantiomers of 3-quinuclidinol are obtained by the procedure of B. Ringdahl, B. Resul and R. Dahlbom [Acta. Pharm. Seuc., 16, 281 (1979)].

The following examples are illustrative of the invention. Temperature is expressed in degrees Celsius; NMR signals are given as ppm downfield from an internal standard of tetramethysilane.

EXAMPLE I 1,4-Dihydro-2,6-dimethyl-4-(3-nitrophenyl)-5-nitropyridine-3-carboxylic Acid To 60 mL of water was added 60 g (0.57 mole) of 1-nitro-2-propanol and 92 g (0.57 mole) of sodium dichromate. The resulting mixture was cooled in an ice bath and a solution of 60 mL of concentrated sulfuric acid in 50 mL of water was added over two hours while the temperature of the reaction mixture was maintained below 10 ° C. The mixture was stirred for an additional five hours, diluted with 600 mL of water and extracted four times with ether. The organic layers were combined and dried over magnesium sulfate. Removal of the solvent gave 62.1 mL of a liquid which crystallized on standing. The resulting solid was recrystallized from ether to give 36.4 g of 1-nitro-2-propanone, $^1$H NMR 5.5 (s, 2H), 2.4 (s, 3H).

To a solution of 64 g (0.42 mole) 3-nitrobenzaldehyde in benzene was added 29.2 g of D-butylamine. The mixture was heated to reflux in a flask equipped with a Dean-Stark trap. After 90 minutes, the theoretical amount of water had separated, and the mixture was cooled and the solvent removed under vacuum, to give 84.4 g of N-(3-nitrobenzylidene)-1-butanamine.

To a solution of 28.6 g (0.39 mole) of the butanamine in 75 mL of acetic anhydride was added 15 g of 1-nitro-2-propanone. A white precipitate formed almost at once. The mixture was warmed gently until the solid dissolved, cooled, stirred for five hours, carefully poured onto water and extracted with ether. The organic layer was separated, washed with water, dried over anhydrous magnesium sulfate and the solvent removed under reduced pressure. After storage at 0° C. overnight, the residue had crystallized. Recrystallization of the resulting solid from dibutyl ether gave 9.3 g of 4-(3-nitrophenyl)-3-nitro-3-buten-2-one, $^1$H NMR 8.4 (m, 2H), 7.7 (m, 2H), 7.5 (s, 1H), 2.5 (s, 3H).

To 10 mL of methanol was added 20 g (0.13 mole) of 2-cyanoethyl acetoacetate. The solution was cooled in ice and a slow stream of ammonia gas was passed through it for five hours. The reaction flask was stoppered and stored at 0° C. overnight. The resulting solid was collected, washed with a small amount of methanol and dried under high vacuum to give 11.1 g (0.072 mole) of 2-cyanoethyl 3-aminobut-2-enoate, $^1$H NMR 4.6 (s, $^1$H), 4.3 (t, 2H), 2.8 (t, 2H), 2.0(t, 3H).

To 100 mL of ethanol was added 11.8 g (0.05 mole) of 4-(3-nitrophenyl)-3-nitro-3-buten-2-one and 7.7 g (0.05 mole) of 2-cyanoethyl-3-aminobut-2-enoate. The mixture was heated at reflux overnight, cooled and filtered. The resulting yellow solid was washed with a small amount of ethanol and dried under high vacuum to give 13.85 g (0.037 mole) of 2-cyanoethyl 1,4-dihydro-2,6-dimethyl-4-(3-nitrophenyl)-5-nitropyridinecarboxylate, $^1$H NMR 10.0 (m, 1H), 8.2 (m, 2H), 7.9 (m, 2H), 5.5 (m, 1H), 4.3 (t, 2H), 3.3 (s, 1H), 2.4 (s, 3H), 2.3 (s, 3H).

To 50 mL of 1,2-dimethoxyethane was added 7.2 g (0.02 mole) of 2-cyanoethyl 1,4-dihydro-2,6-dimethyl-4-(3-nitrophenyl)-5-nitropyridinecarboxylate. To this solution was added dropwise over 15 minutes 23 mL of 1.0M sodium hydroxide. After four hours, the mixture was diluted with water and extracted three times with ethyl acetate. The aqueous layer was separated, made acidic (pH<2) with 2M hydrochloric acid and stored at 0° C. for one hour. The resulting solid was filtered and dried overnight under high vacuum to give 6.1 g (0.018 mole) of yellow solid 1,4-dihydro-2,6-dimethyl-4-(3-nitrophenyl)-5-nitropyridine-3-carboxylic acid. $^1$H NMR 9.2 (m, 1H), 8.2 (s, 1H), 7.8 (m, 2H), 7.5 (m, 2H), 5.4 (s, 1H), 2.5 (s, 3H), 2.2 (s, 3H).

EXAMPLE II (+)-1,4-Dihydro-2,6-dimethyl-4-(3-nitrophenyl)-5-nitropyridine-3-carboxylic Acid To a solution of 14.5 g (0.033 mole) of brucine dihydrate in 300 mL of N-butyl acetate was added 12.5 g (0.033 mole) of 1,4-dihydro-2,6-dimethyl-4-(3-nitrophenyl)-5-nitropyridinecarboxylic acid prepared as described in Example I. The mixture was heated to 100° C. and sufficient methanol (approximately 100 mL) was added to effect solution. The mixture was allowed to stand overnight, filtered and the resulting solid recrystallized twice from butyl acetate/methanol The mother liquors from all recrystallizations were retained. The crystals were dissolved in 25 mL of 2M hydrochloric acid and the mixture extracted twice with ethyl acetate. The organic layers were combined, washed with brine, dried over magnesium sulfate and the solvent removed under reduced pressure to give 4.1 g (0.0129 mole) of (+)-1,4-dihydro-2,6-dimethyl-4-(3-nitrophenyl)-5-nitropyridinecarboxylic acid; $[\alpha]_{20}^D = +24°$.

EXAMPLE III (−)-1,4-Dihydro-2,6-dimethyl-4-(3-nitrophenyl)-5-nitropyridine-3-carboxylic Acid The solvent was removed from the combined mother liquors from the preparation of the (+) isomer as outlined in Example II. The resulting solid was recrystalized once from a mixture of D-butyl acetate and cyclohexane. The crystals thus obtained were recrystallized twice from ethyl acetate/cyclohexane. The resulting solid was dissolved in 2M hydrochloric acid and the mixture extracted twice with ethyl acetate. The organic layers were combined, washed twice with 2M hydrochloric acid, once with brine, and dried over anhydrous magnesium sulfate, to give (−)-1,4-Dihydro-2,6-dimethyl-4-(3-nitrophenyl)-5-nitropyridine-3-carboxylic acid, $[\alpha]_{20}^D = -24.8°$.

EXAMPLE IV (+a, -b)-1-Azabicyclo[2.2.2]oct-3-yl 1,4-Dihydro-2,6-dimethyl-4-(3-nitrophenyl)-5-nitropyridine-3-carboxylate fumarate To 100 mL of methylene chloride was added 2 g (0.00625 mole) of (−)-1,4-dihydro-2,6-dimethyl-4-(3-nitrophenyl)-5-nitro-3-pyridinecarboxylic acid, 1.7 g (0.0065 mole) of triphenylphosphine and 1.4 g (0.0065 mole) of dipyridinyl disulfide. The resulting mixture was stirred overnight at room temperature, the solvent was removed under reduced pressure and the residue chromatographed on activity III alumina with ethyl acetate as the eluent. To 100 mL of methylene chloride was added this thioester and 1.0 g (0.0078 mole) of (+)-1-azabicyclo[2.2.2]octan-3-ol [B. Ringdahl et al., Acta. Pharm. Seuc., 16, 281 (1979); L. H. Sternbach and S. Kaiser, J. Am. Chem. Soc., 74, 2215 (1952)]. A solution of 2.6 g (0.013 mole) of silver tetrafluoroborate in 100 mL of benzene was added. The mixture was stirred overnight and partitioned between methylene chloride and saturated aqueous sodium bicarbonate. The organic layer was separated, dried over anhydrous magnesium sulfate and the solvent removed under reduced pressure. Chromatography of the residue on activity III alumina, eluted with a gradient of ethyl acetate to 5% methanol in ethyl acetate, gave 350 mg of coupled ester. This material was dissolved in 18 mL of boiling 2-propanol, and 0.25 g of fumaric acid was added. After cooling overnight, the solution was again heated to reflux and 3 mL of cyclohexane was added and the mixture allowed to cool. The crystals were collected by filtration and dried under high vacuum, to give 262 mg of (+a, −b)-1-Azabicyclo[2.2.2]oct-3-yl 1,4-Dihydro-2,6-dimethyl-4-(3-nitrophenyl)-5-nitropyridine-3-carboxylate fumarate, mp 144°–147° C. $^1$H NMR (DMSO-d6) 8.1 (m, 2H). 7.65 (m. 2H), 6.6 (s, 2H), 5.4 (s, 1H), 4.9 (m, obscured by HOD). 3.2–2.1 (m, 12H), 2.1–1.5 (m, 5H); IR (KBr) 2945, 1710, 1530 cm$^{-1}$; HPLC (40:15:25, MeOH: THF: H$_2$O, 5 mM heptanesulfonic acid) Tr=11.4 minutes, Kp=3.5, Whatman partisil 10-ODS-2, 1 mL/minute; $[\alpha]_{20}^D = 95.6°$ (c=0.90, MeOH); Anal calcd for $C_{21}H_{24}N_4O_6$ $C_4H_4O_4 \cdot 0.5$ $H_2O$: C, 54.25; H, 5.28; N, 10.11. Found: C, 53.92; H, 5.32; N, 9.86.

EXAMPLE V (−a, −b)-1-Azabicyclo[2.2.2]oct-3-yl 1,4-Dihydro-2,6-dimethyl-4-(3-nitrophenyl)-5-nitropyridine-3-carboxylate fumarate This compound was prepared from (+)-1-azabicyclo[2.2.2]octan-3-ol [B. Ringdahl et al., Acta. Pharm Seuc , 16, 281 (1979); L. H. Sternbach and S. Kaiser, J. Am. Chem. Soc., 74. 2215 (1952)] and (−)-1,4-dihydro-2,6-dimethyl-4-(3-nitrophenyl)-5-nitropyridine-3-carboxylic acid (Example III) according to the procedure described in Example IV to give (−a, −b)-1-Azabicyclo[2.2.2]oct-3-yl 1,4-Dihydro-2,6-dimethyl-4-(3-nitrophenyl)-5-nitropyridine-3-carboxylate fumarate, mp 141°–142° C. $^1$H NMR (DMSO-$d_6$) 8.1 (m, 2H), 7.7 (m, 2H), 6.6 (s, 2H), 5.5 (s, obscured by HOD). 4.9 (m, obscured by HOD), 3.5–2.2 (m, 12H), 2.1–1.5 (m, 5H); IR (KBr) 2945, 1710, 1530 cm$^{-1}$; HPLC (40:15:25, MeOH: THF: $H_2O$, 5 mM heptanesulfonic acid) Tr=11.4 minutes. Kp=3.5, Whatman partisil 10-ODS-2, 1 mL/minute; $[\alpha]_{20}^D = +85.6°$ (c=1.25, MeOH). Anal. calcd for $C_{21}H_{24}N_4O_6$ $C_4H_4O_4$: C, 55.14; H, 5.18; N, 10 28. Found; C, 54.90; H, 5.29; N, 10 14.

EXAMPLE VI (+a, +b)-1-Azabicyclo[2.2.2]oct-3-yl 1,4-Dihydro-2,6-dimethyl-4-(3-nitrophenyl)-5-nitropyridine-3-carboxylate fumarate This isomer was prepared from (+)-1-azabicyclo[2.2.2]octan-3-ol [B. Ringdahl et al., Acta Pharm. Seuc., 16, 281 (1979); L. H. Sternbach and S. Kaiser, J. Am. Chem. Soc.. 74. 2215 (1952)] and (+)-1,4-dihydro-2.6-dimethyl-4-(3-nitrophenyl)-5-nitropyridine-3-carboxylate (Example II) according to the procedure described in Example IV to give (+a, +b)-1-Azabicyclo[2 2]oct-3-yl 1,4-Dihydro-2,6-dimethyl-4-(3-nitrophenyl)-5-nitropyridine-3-carboxylate fumarate, mp 154°–156° C.; $^1$H NMR (DMSO-$d_6$) 8.1 (m, 2H), 7.6 (m, 2H), 6.5 (s, 1H), 5.4 (s, 1H), 4.8 (m, obscured by HOD) 3.4–2.1 (m. 12H), 2.1–1.5 (m, 5H); IR (KBr) 2960, 1710 cm$^{-1}$; HPLC (40:15:25, MeOH: THF: $H_2O$, 5 mM heptanesulfonic acid) Tr=11.2 minutes, Kp=3.48, Whatman partsil 10-ODS-2, 1 mL/minute; $[\alpha]_{20}^D = -87.4°$ (c=1.75, MeOH). Anal. calcd for $C_{21}H_{24}N_4O_6$ $C_4H_4O_4$: C, 55.14; H, 5.18; N, 10.28. Found: C, 55.36; H, 5.31; N, 10.49.

EXAMPLE VII (−a, +b)-1-Azabicyclo[2.2.2]oct-yl 1.4-Dihydro-2,6-dimethyl-4-(3-nitrophenyl)-5-nitropyridine-3-carboxylate fumarate This isomer was obtained from (−)-1-azabicyclo[2.2.2]octan-3-ol [B. Ringdahl et al., Acta. Pharm. Seuc., 16, 281 (1979); L. H. Sternbach and S. Kaiser, J. Am. Chem. Soc., 74, 2215 (1952)] and (+)-1,4-dihydro-2,6-dimethyl-4-(3-nitrophenyl)-5-nitropyridine-3-carboxylic acid (Example II) according to the procedure described in Example IV. The fumarate melted at 152°–156° C.; $^1$H NMR (DMSO-$d_6$) 8.1 (m, 2H), 7.6 (m, 2H), 6.6 (m, 2H), 5.4 (s, 1H), 4.75 (m, obscured by HOD). 3.2–2.1 (m, 12H), 2.1–1.3 (m, 5H); IR (KBr) 2954, 1708 cm$^{-1}$; HPLC (40:15:25, MeOH: THF: $H_2O$, 5 mM heptanesulfonic acid) Tr=11.6 minutes, Kp=3.64, Whatman partisil 10-ODS-2, 1 mL/minute; $[\alpha]_{20}^D - 97.6°$ (c=12.15 MeOH). Anal. calcd for $C_{21}H_{24}N_4O_6$ $C_4H_4O_4$: C, 55.14; H, 5.18; N, 10.28. Found: C. 55.04; H, 5.40; N, 10.31.

EXAMPLE VIII

Potentiation of Calcium Influx across the Membrane

This test system was developed to evaluate the relative ability of compounds to potentiate calcium influx into cells via voltage sensitive calcium channels. The technique employs a high calcium affinity fluorescent dye to monitor changes in intracellular free calcium concentrations. The cells are incubated with a protected non-fluorescent form of the calcium sensitive dye. This compound permeates the cell wall and enters the cell. There it is transformed by enzymes into the fluorescent dye Quin 2 which cannot leave the cell Quin 2 has a high affinity for calcium ions and when calcium is bound to the dye, the complex fluoresces, the intensity of the fluorescence being proportional to the concentration of calcium ions. Voltage sensitive calcium channels are activated by the addition of potassium chloride to the media and calcium ion influx occurs. The increase in fluorescence is measured, giving a relative measure of calcium influx, the control value. In a separate cuvette, both potassium chloride and the test compound are administered to the cells and the fluorescence measured. A calcium agonist should increase influx of calcium into the cells and therefore an increase in the fluorescence. The percent stimulation above control is obtained from the increase in fluorescence.

Differentiated murine neuronal (neuroblastoma x glioma) hybrid cells (NGI08-15) which contain an abundance of voltage dependant calcium channels were used as a source of tissue for testing these compounds.

Briefly, NGI08-15 cells were cultured in 10% $CO_2$ at 37° C. in Dulbecco's modified Eagle's medium (DMEM) supplemented with glutamine (1.0 mM). fetal bovine serum (FBS; 10%). and hypoxanthine (100 $\mu$M), aminopterin (1.0 $\mu$M). and thymidine (20 $\mu$M). Differentiation was induced by treatment with dibutyl cyclic AMP (4 days, 1.0 mM) [L. Noronha-Blob, C. Richard and D. U'Prichard, J. Neurochem , 50, 1381–1390, 1988]. The cells were harvested by gentle agitation in warm D1 saline (composition: 137 mM NaCl, 5.4 mM KCl, 0.17 mM $Na_2PO_4$, 0.22 mM $KH_2PO_4$, 5.5 mM glucose). Dispersed cells (5×10$^6$ cells/mL) were incubated with quin 2 acetoxymethyl ester (quin 2-AM, the calcium specific dye) [100 $\mu$M. in dimethyl sulfoxide (DMSO)] for 60 minutes at 37° C. The control suspensions received only DMSO. Cells were then diluted in ice-cold media, centrifuged and washed twice (1,500×g, 3 minutes) in ice-cold HEPES buffer (composition: 130 mM NaCl, 5.0 mM KCl, 6.0 mM glucose, 1.0 mM $MgCl_2$, 1.0 mM $CaCl_2$, and 20 mM HEPES, pH 7 4).

Fluorescence was monitored on a Perkin-Elmer LS-5 Spectrophotometer at excitation and emission wavelengths of 339 and 492 nm, 15 and 20 nm slit width, respectively. Cells (~3×10$^6$/cuvette) were kept in suspension at 37° C. with a magnetic cell stirrer Depolarization was induced with KCl (50 mM), or where indicated by concurrent additions of KCl and the calcium agonist, BAY K 8644. The change in fluorescence was calculated from the difference between final and initial values. The results were expressed as a percent enhancement over potassium chloride stimulation (control).

The results of these tests are shown in Table I.

TABLE I

| Formula I Isomers | Agonist Activity % Stimulation Above Control |
|---|---|
| (−a, −b) | 10 |
| (−a, +b) | 25 |
| (+a, −b) | 31 |
| (+a, +b) | 20 |
| BAY K 8644 (Reference Standard) | 38 |

EXAMPLE IX

Enhancement of Calcium Ion Evoked Smooth Muscle Contractility

This test is a measure of the ability of test compounds to enhance muscle contraction caused by calcium ions. A sample of muscle was placed under tension in a device to measure its length and contracted by addition of potassium chloride (to activate the calcium channels) followed by addition of a calcium ion solution. The addition of a calcium agonist should cause the influx of additional calcium ions and thereby cause further contraction of the muscle. The lowest concentration of test compound necessary to evoke this additional contraction was measured, as were the maximum contraction obtained and the concentration at which it was reached The ileum of male albino guinea pigs were cut into 3–4 cm segments. The longitudinal muscle, with myenteric plexus attached, was separated from the circular muscle. The tissue were suspended in 10 mL water jacketed glass tissue baths containing Tyrodes solution (137 mM sodium chloride, 2.7 mM potassium chloride, 1.8 mM calcium chloride, 1.1 mM magnesium chloride, 0.4 mM sodium dihydrogen phosphate, and 5.6 mM dextrose). The baths were maintained at 37° C. and aerated with 95% oxygen/5% carbon dioxide. Each preparation was suspended under resting tension of 0.3 g. The tissues were switched to calcium free Tryodes solution for 24 minutes. with complete replacement of the solution every four minutes. Potassium chloride was then added to produce a bath concentration of 80 nM, and calcium solutions were cumulatively added to increase the bath calcium ion concentration to 0.2–8.0 mM. The tissues were re-equilibrated in normal Tyrodes and then calcium free Tyrodes. Enhancement of calcium evoked contractions in the presence of drug were determined by repeating the cumulative addition procedure after the tissues were exposed to the drug for six minutes. Responses were expressed relative to the maximum contraction elicited by calcium ion in the absence of the drug. The data from this experiment is shown in Table II The threshold for enhancement is the lowest concentration of compound that produced enhancement of the calcium evoked contraction The maximum enhancement is the increase above control responsiveness expressed as a percent of the maximum control calcium evoked contraction Also listed are the concentration of compound that produced the maximum enhancement.

TABLE II

| Formula I Isomers | Threshold for Enhancement (nM) | Maximum Enhancement (% maximum contraction) | Concentration at Maximum Enhancement (nM) |
|---|---|---|---|
| (−a, −b) | 10 | 18% | 10 |
| (−a, +b) | 100 | 13% | 1000 |
| (+a, −b) | 10 | 15% | 10 |
| (+a, +b) | 10 | 11% | 100 |
| BAY K 8644 (Reference Standard) | 10 | 38% | 100 |

What is claimed:

1. A compound of the formula:

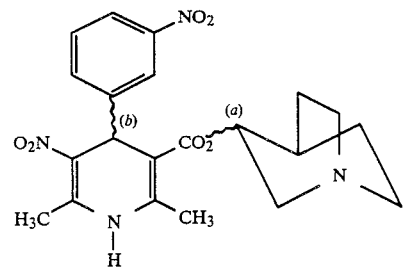

in which (a) and (b) are asymmetric centers which may be the same or different and have either the absolute R or S configuration.

2. The compound of claim 1 wherein the center (a) is dextrorotatory and the center (b) is levorotatory.

3. The compound of claim 1 wherein the (a) and (b) centers are levorotatory.

4. The compound of claim 1 wherein the (a) and (b) centers are dextrorotatory.

5. The compound of claim 1 wherein the center (a) is levorotatory and the center (b) is dextrorotatory 6. A pharmaceutical composition comprising the compound of claim 1 and a pharmaceutically acceptable carrier.

7. A method for producing cardiotonic activity comprising administering to a host in need of treatment an effective amount of the composition of claim 6.

8. A method for treating congestive heart failure comprising administering to a host in need of treatment an effective amount of the composition of claim 6.

* * * * *

UNITED STATES PATENT AND TRADEMARK OFFICE
CERTIFICATE OF CORRECTION

PATENT NO. : 4,975,437

DATED : December 4, 1990

INVENTOR(S) : John P. Carter and Waclaw J. Rzeszotarski

It is certified that error appears in the above-identified patent and that said Letters Patent is hereby corrected as shown below:

At column 4, line 32, and again at column 5, line 2, the patent reads "D-butylamine" and should read --n-butylamine--. At column 5, line 59, the patent reads "N-butyl" and should read --n-butyl--. At column 6, line 15, the patent reads "D-butyl" and should read --n-butyl--. At column 6, line 64, the patent reads "HOD)." and should read --HOD),--. At column 7, line 8, the patent reads "(+)-1-" and should read -- (-)-1- --. At column 7, line 38, the patent reads "[2 2.2]" and should read --[2.2.2]--. At column 8, line 5, the patent reads "the Membrane" and should read --the Plasma Membrane--. At column 8, line 39, the patent reads "(1.0 µM)." and should read --(1.0 µM),--. At column 9, line 26, the patent reads "reached" and should read --reached.--.

Signed and Sealed this

Twenty-second Day of December, 1992

Attest:

DOUGLAS B. COMER

Attesting Officer

Acting Commissioner of Patents and Trademarks